United States Patent [19]

Pappas

[11] Patent Number: 5,178,626
[45] Date of Patent: Jan. 12, 1993

[54] STEPPED SURGICAL SAW BLADE

[76] Inventor: Michael J. Pappas, 61 Gould Pl., Caldwell, N.J. 07006

[21] Appl. No.: 607,845

[22] Filed: Nov. 1, 1990

Related U.S. Application Data

[63] Continuation of Ser. No. 296,602, Jan. 13, 1989, abandoned.

[51] Int. Cl.⁵ .............................................. A61B 17/14
[52] U.S. Cl. ...................................... 606/178; 30/350; 83/835
[58] Field of Search ................... 606/82, 87, 176, 178, 606/177; 30/348, 350, 351; 83/835

[56] References Cited

U.S. PATENT DOCUMENTS

| | | | |
|---|---|---|---|
| 3,943,934 | 3/1976 | Bent | 30/339 |
| 4,036,236 | 7/1977 | Rhodes, Jr. | 128/317 |
| 4,513,742 | 4/1985 | Arnegger | 83/835 |
| 4,584,999 | 4/1986 | Arnegger | 128/317 |
| 4,617,930 | 10/1986 | Saunders | 128/317 |
| 4,703,751 | 11/1987 | Pohl | 128/92 VY |
| 4,718,413 | 1/1988 | Johnson | 128/92 VY |
| 4,750,481 | 6/1988 | Reese | 128/92 V |

Primary Examiner—C. Fred Rosenbaum
Assistant Examiner—William W. Lewis
Attorney, Agent, or Firm—John D. Kaufmann; John G. Gilfillan, III

[57] ABSTRACT

A surgical saw having a base blade portion, a plurality of staggered teeth and an intermediate blade portion, the thickness of which is less than the thickness of the base blade portion. The thickness of the intermediate blade portion is sufficiently less than the thickness of the base blade portion to permit passage of bone cuttings and other material away from the staggered teeth during operation of the surgical saw.

8 Claims, 1 Drawing Sheet

STEPPED SURGICAL SAW BLADE

This application is a continuation of application Ser. No. 07/296,602 filed Jan. 13, 1909, now abandoned.

BACKGROUND OF THE INVENTION

This invention relates to surgical instruments. In particular this invention relates to saw blades for making surgical cuts.

Surgical saw blades for use with powered surgical saws are well known. Generally they are relatively thin (approximately 0.030 inches) surgical steel elements having staggered teeth on a cutting edge. The degree of stagger is often approximately half the material thickness, i.e. 0.015 inches above the plane of the top surface of the saw blade and 0.015 inches below the plane of the bottom surface of the surgical saw. Thus, because of the stagger, a saw which is 0.030 inches in thickness ordinarily makes a cut which is at least 0.060 inches thick.

Surgical saws so structured have presented a plurality of problems. When used with a flat guide surface then tend to flex in response to the efforts of the surgeon to hold the blade flat on the guide surface. The problem of flexing is particularly troublesome when the surgeon is performing "skimming" cuts, i.e. cuts where only very slightly thicknesses of bones are to be removed. Thin surgical saw blades tend to flex and be deflected away from the desired plane of the cut. Such flexion results in surgical difficulties and worse, may result in uneven resectioned surfaces.

Another problem with the known blade structures is that they are not conductive for use with capture slot type guides, i.e. guides which are defined by slots rather than uni-planar surfaces. Where such slots are closed-ended, because of the saw tooth's stagger, the slot width must be substantially greater than the thickness of the blade so as to permit passage of the toothed portion therethrough.

Even when a capture slot is open at one end, the slot width must be substantially greater than the blade thickness or the guide containing the slot must be positioned away from the bone being resectioned to permit room for the staggered teeth of the blade to be introduced between the bone to be cut and the guide. Such displacement of the guide from the bone to be cut is recognized by most surgeons to be undesirable.

An apparently obvious solution to the flexion problem is to increase the blade thickness. In prior blade design philosophy, however, increasing the blade thickness was unacceptable because as the blade thickness increased, so did the tooth stagger tooth size and cut width. Thick staggered teeth are known to increase cutting effort and to generate excessive heat during cutting. Neither of these conditions is desirable.

SUMMARY OF THE INVENTION

It is an object of the present invention, therefore, to provide a surgical saw blade which is resistant to flexion during operation.

Another object of the present invention is to provide a surgical saw blade which does not require unnecessary cutting force to be applied by the surgeon.

A further object of the present invention is to provide a surgical saw blade which does not generate unacceptable levels of heat during cutting.

An additional object of the present invention is to provide a surgical saw blade which is suitable for use with a capture slot type guide.

Still a further object of the present invention is to provide a surgical saw having means to permit bone cuttings or other material to pass freely away from the saw.

These and other objects are enumerated are achieved by the surgical saw blade of the present invention, one embodiment of which may include a base blade portion of a first thickness, a staggered tooth portion the thickness of which is substantially equal to the thickness of the base blade portion, and an intermediate blade portion connecting the base blade portion and the staggered tooth portion, the intermediate blade portion being of a thickness less than the thickness of the base blade portion or the staggered tooth portion.

BRIEF DESCRIPTION OF THE DRAWING

A more complete understanding of the present invention may be had from the following detailed description thereof, particularly when read in view of the attached drawing, wherein.

DETAILED DESCRIPTION

Figure 1:
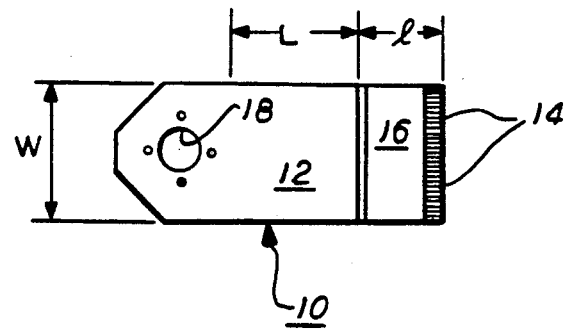
FIG. 1 is a plan view of a surgical saw blade structured according to the present invention.
Figure 2:
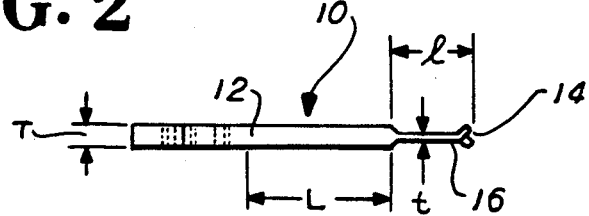
FIG. 2 is a side view of the saw blade of FIG. 1.

Referring therefore to FIGS. 1 and 2, a surgical saw balde structured in accordance with the teaching of the present invention is shown and designated generally by the reference numeral 10.

Saw blade 10 can be seen to include a base blade portion 12, a plurality of staggered teeth 14 and an intermediate blade portion 16. Provided at the end of saw blade 10 which is remote from staggered teeth 14 are a plurality of openings 18 which will be recognized by those skilled in the arts to define a securing means whereby saw blade 10 may be locked to a surgical saw power unit (not shown).

The width of saw blade 10 is uniform and designated here by letter "w." The area of the blade portion 12 of saw blade 10 between the openings 18 and the intermediate portion 16 and unsupported by the power unit is disclosed to be of a length "$L_1$" with a thickness designated by the letter "T". A typical thickness for such a saw blade would be where the dimension "T" is approximately 0.060 inches. In this regard, it has been found that such a thickness is sufficient to avoid most of the flexion problems discussed above with respect to prior art blades.

The intermediate blade portion 16 is shown to be of a length "$L_2$" and a thickness designated by the letter "t". It has been found that a saw having a base blade thickness of 0.060 inches is well served by an intermediate blade portion 16 which is 0.030 inches thick. In this regard, where intermediate blade portion 16 is 0.030 inches thick, the dimension from the top edges of staggered teeth 14 to the bottom edges of staggered teeth 14 may be equal to or slightly greater than double the thickness "t", i.e. equal to or slightly greater than the thickness "T". It has also been found that it is desirable that the length "$L_2$" be no greater than the length "$L_1$"

to avoid undesirable flexions although preferably length "L₂" should be only long enough to allow the passage of bone cuttings.

Reduction of the thickness of saw blade 10 so as to define intermediate blade portion 16 provides two benefits. First, it permits the formation of staggered teeth 14, such as by stamping so as to result in a tooth depth, i.e., the distance from the top edges of the upwardly extending staggered teeth 14 to the bottom edges of downwardly extending staggered teeth 14, which may be equal to or slightly greater than the thickness "T" of base blade portion 12. Where larger or smaller tooth depths are desired, the forming technique can be adjusted accordingly. Secondly, the reduced thickness of the intermediate blade portion 16 provides a space into which cutting chips may be released from the saw teeth. This is particularly beneficial where the cutting blade 10 extends into the member being cut. In such instances, the cutting chips are displaced away from the teeth 14 and pass transversely of the blade out of the resected area. The clearing of the chips, of course, is assisted by the motion of the blade.

The advantage of surgical saw blades structured in accordance with the present invention is that the thickness of the base blade portion 12 provides resistance to deflection while the reduced thickness of the intermediate blade portion 16 permits forming of the staggered teeth at any desired thickness, including a thickness equal to or less than the thickness of the base blade portion 12. Further, the reduced thickness of the intermediate blade portion 16 facilitates removal of cutting chips, as discussed above.

Saw blade 10 may be manufactured using any of the many materials known to those skilled in these arts. Further, saw blade 10 may be manufactured using any of the manufacturing techniques known to those skilled in these arts.

Figure 3:
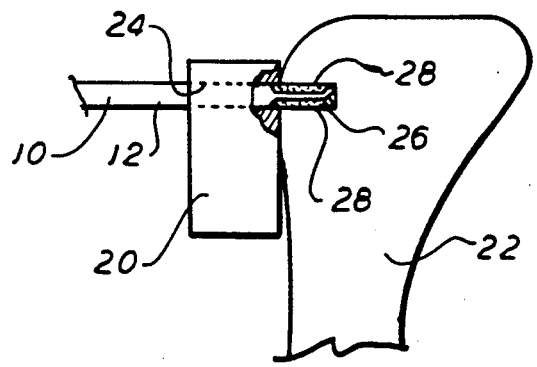
FIG. 3 is an elevational view, partially in cross-section of a surgical saw blade utilized with a capture slot type surgical cutting guide to resection a bone.
Figure 4:
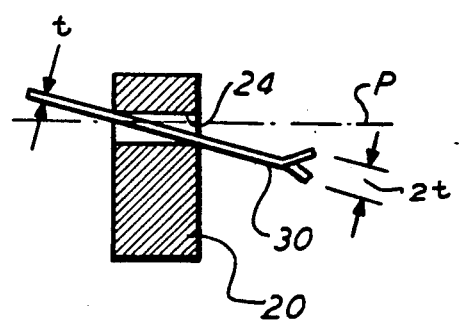
FIG. 4 is an elevational view, partly in cross-section, of a prior art device.

The true advantages of saw blade 10 best may be seen with reference to FIGS. 3 and 4. More specifically, FIG. 3 shows a saw blade 10 in use with a cutting guide 20 to cut a bone such as a tibia 22. Cutting guide 20 is provided with a capture slot 24 through which blade 10 is inserted. FIG. 4 shows a prior art saw 30 in capture slot 24. Both saws 10 and 30 have identical tooth portion thickness "2t." With the conventional saw 30 since the slot 24 is much wider than the thickness "t," the saw 30 is free to move out of the guide plane "P" and thus can produce a resection plane substantially different than desired.

As best may be seen from FIG. 3, the height "H" of capture slot 24 is only very slightly greater than the thickness "T" of the base blade portion 12 of saw 10. Thus, blade 10 is supported against flexion by both the upper and lower surfaces of the capture slot 24. Also, the depth "D" of the capture slot 24 is substantial. Additionally, the length "L₂" of the intermediate portion 16 should be substantially less than the depth of the capture slot 24 so that there will be sufficient support for the base blade portion 12 by slot 24. Since L₂ is substantially less than the depth of the capture slot 24 and since the depth of the capture slot is less than L₁, L₂ is much less than L₁.

As blade 10 forms a cut 26 in the bone 27, chips or bone fragments 28 resulting from the cutting are carried away from the cutting face and are carried out of the cutting area by the oscillation of the cutting blade 10. As a result the cutting face is maintained clean and the cutting process can continue without reservation as to interference from build-up of chips 28.

The stiffness of the saw blade 10 may be adequately computed using the simple cantilever beam bending equation which for this case is:

$$K = EwT_e^3/4(L_1+L_2)^3$$

where
K = stiffness of the saw blade 10
$T_e$ = effective thickness of saw 10 where "$T_e$" is less than "T" and greater than "t" and where "$T_e$" is a function of "$L_1$" and "$L_2$"
w = width of saw 10
($L_1 + L_2$) = unsupported length of saw 10
E = the material stiffness (Young's modulus)

From this equation it may be seen that given a particular saw length ($L_1+L_2$) and width "w" that a saw 10 having an effective thickness "$T_e$" equal to 0.060 inches is eight times stiffer than a saw 0.030 inches thick, which is typical for surgical saws. Since the stiffness "K" is proportional to the unsupported length cubed, $(L_1+L_2)^3$, when the length "L₂" of portion 16 is made small, but sufficient to clear bone cutting chips 28, the effective thickness "$T_e$" will approach "T" and the portion 16 will have little effect on overall stiffness "K." Thus a saw blade 10 of the type taught here can be made approximately eight times stiffer than a conventional saw while still retaining the cutting characteristics of the conventional saw with respect to cut width, forces and heat generation.

Conventional saws have been observed to bend more than 0.080 inches during resection producing cuts which thus differed from the desired resection plane by that amount. This level of error is undesirable and often unacceptable. An acceptable error for many applications, such as preparation of flat surfaces to receive prostheses loading surfaces, is about 0.020 inches or one quarter the observed amount. Thus a saw stiffness "K" of about four times the stiffness of a typical conventional saw is highly desirable for many applications. Such stiffness "K" can be achieved with the type of saw taught here even where the length "L₂" of the intermediate portion 16 is approximately the same length as the base portion 12. Thus from a stiffness perspective one can produce a saw blade 10 of satisfactory stiffness "K" where the length "L₁" of the base portion 12 is approximately equal to the length "L₂" of the intermediate portion 16.

Where the saw blade 10 is used in conjunction with the guide 20, however, it is desirable to use a relatively short, thin portion 16 so that the thicker portion 12 can act as a uniform guiding surface during the resection procedure. Thus the length "L₂" of the thin portion 16 should generally be much less than the width of the guide 20 with which it is used.

There are two further advantages to the saw blade 10 taught here. First, as a result of the increased stiffness of the saw blade 10 it is possible now to produce a saw 10 of adequate stiffness which makes a thinner cut and uses finer teeth 14 (the tooth size is dependent on the saw thickness "t" increasing with increasing thickness), thereby producing a saw blade 10 which requires less force to produce a resection and which generates less heat during resection. For example, if one can produce a saw blade 10 that is eight times stiffer than a conventional saw, and if a saw of only four times greater stiffness is needed for a given application, one can then make a saw for this application according to this teaching which has the desired stiffness "K" but which will make a thinner cut than a conventional saw with its attendant benefits. Further, in those cases where a conventional saw is of adequate stiffness then it is possible, using these teachings, to produce a saw which will make a cut only half the thickness of a cut made by a conventional saw thereby greatly reducing needed cutting forces and bone damaging heat.

Second, the thick portion 12 helps guide the saw blade 10 even in the absence of a guide 20. Frequently in cutting bones, the surgeon first uses a guide 20 to help made a partial cut. The guide 20 is then removed and the partial cut is used as a "meter box" to guide the saw 10 to complete the cut. In this situation, the partial cut acts like a capture slot in a guide instrument and thus for the same reasons that the saw 10 taught here provides greater cutting precision when used with the capture slot 24, it provides greater cutting precision when used with the partial cut "miter box." Further, a stiffer saw 10 requiring less cutting force than a conventional saw is easier to direct and control than a conventional saw.

It is clear, therefore, that the surgical saw blade 10 of the present invention provides a structure which is resistant to undesirable flexion and which also may be utilized with capture slots without the attendant problems set out above.

However, it will be recognized by those skilled in these arts that many modifications and variations to the present invention may be made without departing from the spirit and scope of this application.

We claim:

1. A surgical saw blade comprising:
   a base blade portion having a thickness and having upper and lower surfaces, said base blade portion including a supported length which is adapted to be engaged by and supported by an operating means such as a saw head, and an unsupported length, the upper and lower surfaces of said unsupported length defining generally parallel planes such as to comprise guide surfaces for cooperating either with surfaces of a guide slot or with a guide slot and the surfaces of a resected bone to guide said saw blade;
   a plurality of teeth disposed on the end of said blade distant from said base blade portion, some of said plurality of teeth having upper tips falling substantially within the plane of said upper surface of said unsupported length and other of said plurality of teeth having lower tips falling substantially within the plane of said lower surface of said unsupported length; and
   an intermediate blade portion disposed between said teeth and said base plate portion, the thickness of said intermediate blade portion being less than the thickness of said base blade portion, and the length of said intermediate blade portion being less than the unsupported length of said base blade portion.

2. A surgical saw blade according to claim 1 wherein the thickness of said intermediate blade portion is sufficiently less than the thickness of said base blade portion to permit passage of cuttings away from said teeth during operation of said surgical saw when said teeth are disposed within a member being cut.

3. A surgical saw blade according to claim 1 wherein the length of said intermediate blade portion is sufficiently small to insure that said upper and lower surfaces of said base blade portion are in guiding relationship with either said guide slot or said surfaces of a resected bone at all times during operation of said saw blade.

4. A surgical saw blade according to claim 1 wherein the length of said intermediate blade portion is sufficiently small to have little effect on the overall stiffness of the saw blade.

5. A surgical saw blade for use with a power unit, comprising:
   a planar base portion having a first thickness extending between two parallel surfaces, a first length which is perpendicular to the first thickness and the surfaces and which extends away from a side adapted to be supported by the power unit, and a first width across the surfaces which is perpendicular to the first thickness and the first length;
   a continuous intermediate portion having a second thickness and having a width equal to the first width, the intermediate portion being integral with the base portion remote from the site and along the width and containing no holes or voids, the intermediate portion having a second length, the second thickness being less than or equal to about one-half of the first thickness, the second length being less than the first length; and
   a plurality of alternatively staggered teeth formed in the free edge of the intermediate portion opposite the site and along the width, adjacent teeth having tips spaced apart along the thickness which are co-planar with the surfaces of the base portion.

6. A surgical saw blade as in claim 5, wherein:
   the surfaces are engageable by the walls of a guide slot and the surfaces of a resected bone to guide the blade.

7. A surgical saw blade as in claim 5, wherein:
   the stiffness of the blade is primarily dependent on the first thickness.

8. A surgical saw blade as in claim 5, wherein:
   the second length is substantially less than the first length.

* * * * *